US007285105B2

(12) United States Patent
Kim et al.

(10) Patent No.: US 7,285,105 B2
(45) Date of Patent: *Oct. 23, 2007

(54) AUTOMATIC DIALYZER AND DIALYZING METHOD

(75) Inventors: Sung-Teh Kim, Kitakyushu (JP);
Masahiro Taoka, Kitakyushu (JP);
Tieko Yamamoto, Kitakyushu (JP);
Kunihiko Yamanaka, Kitakyushu (JP);
Katunori Masaoka, Yamagata-gun (JP)

(73) Assignees: JMS Co., Ltd, Hiroshima-shi, Hiroshima (JP); KitaKyusha Institute of Biophysics Co., Ltd, KitaKyushu-Shi, Fukuoka (JP)

( * ) Notice: Subject to any disclaimer, the term of this patent is extended or adjusted under 35 U.S.C. 154(b) by 556 days.

This patent is subject to a terminal disclaimer.

(21) Appl. No.: 10/311,391

(22) PCT Filed: Jun. 14, 2001

(86) PCT No.: PCT/JP01/05076

§ 371 (c)(1),
(2), (4) Date: Mar. 11, 2003

(87) PCT Pub. No.: WO01/95955

PCT Pub. Date: Dec. 20, 2001

(65) Prior Publication Data

US 2003/0163077 A1 Aug. 28, 2003

(30) Foreign Application Priority Data

Jun. 15, 2000 (JP) .............................. 2000-180640
Jun. 14, 2001 (JP) .............................. 2001-179552

(51) Int. Cl.
*A61M 37/00* (2006.01)
*B01D 11/00* (2006.01)
*C02F 1/44* (2006.01)
*C02F 9/00* (2006.01)
*A61M 1/16* (2006.01)

(52) U.S. Cl. ..................... 604/5.04; 604/5.01; 604/6.1; 604/6.11; 604/6.16; 210/646; 210/650; 210/195.2; 210/257.2; 128/DIG. 3

(58) Field of Classification Search ............... 604/4.01, 604/5.01–5.04, 6.09, 6.1, 6.11, 6.15, 6.16; 128/DIG. 3; 210/645–647, 650–652, 739, 210/741, 85–87, 194, 195.1–195.2, 197, 210/198.1, 200, 203, 252, 258, 260
See application file for complete search history.

(56) References Cited

U.S. PATENT DOCUMENTS 5,011,607 A 4/1991 Shinzato ..................... 210/637
5,662,806 A * 9/1997 Keshaviah et al. ......... 210/739

FOREIGN PATENT DOCUMENTS

JP 04371164 A 12/1992

(Continued)

OTHER PUBLICATIONS

Kyushu HDF investigative Commission's Bulletin, "Purification of Blood and Water", 1, 33-42, 1995 p. 33, lines 6 to 16 Abstract Only.

*Primary Examiner*—Patricia Bianco
(74) *Attorney, Agent, or Firm*—L.C. Begin & Associates, PLLC.

(57) ABSTRACT

An automatic dialyzer for purifying blood brought into contact with a dialysate via a semi-impermeable membrane. The dialyzer includes at least a blood circulating system and a dialysate supply/discharge system, wherein the blood line of the blood circulating system is connected to an overflow line having a reversibly-rotatable blood pump, a blood chamber, and an open/close device for overflowing of liquid from the blood chamber to the outside of the blood line. Liquid supply means is provided to a first bypass line and/or a second bypass line for supplying liquid in both forward and reverse directions to enable regulation of the supply amount of the dialysate for water removing/liquid replenishing. The supply speed of the liquid supply device and the supply speed of the blood pump are regulatable in conjunction with each other. Also provided is a dialyzing method using the automatic dialyzer.

19 Claims, 4 Drawing Sheets

FOREIGN PATENT DOCUMENTS

| | | |
|---|---|---|
| JP | 5-19075 | 5/1993 |
| JP | 06114102 A | 4/1994 |
| JP | 7-44915 | 12/1995 |
| JP | 08038597 A | 2/1996 |
| JP | 2000-325470 | * 11/2000 |

* cited by examiner

AUTOMATIC DIALYZER AND DIALYZING METHOD

TECHNICAL FIELD

The present invention relates to a hemodialyzing apparatus and a hemodialyzing method whereby a series of operations including hemodialysis and corresponding preparation/recovery operations are automated as much as possible for savings in labor.

BACKGROUND ART

A hemodialyzer is medical equipment for purifying the blood of renal failure patients and drug intoxication patients. The mechanism for hemodialysis treatment generally consist of three parts: a hemodialyzer, a blood line through which blood circulates, and a dialysate supply system. While maintaining an extracorporeal circulation by means of a blood line which is directly connected to the inside of the blood vessel at two locations, the blood is fed into the compartment inside a hollow fiber of the hemodialyzer, which is connected to some midpoint in the blood line.

On the other hand, an electrolyte called dialysate is flown into the compartment outside the hollow fiber of the hemodialyzer in the opposite direction of the blood flow. Both compartments of the hemodialyzer are divided by a separation membrane called hemodialysis membrane, and while the blood and dialysate flow in opposite directions, material transfer by diffusion occurs depending on the density gradient across the separation membrane, and thus removal of uremic toxin and intoxicating substances as well as replenishing of substances in shortage are performed. Generally, the above described hemodialyzing apparatus is composed of equipment for maintenance of extracorporeal circulation, stable supply of dialysate, control of excess water removal from blood, and the like.

In view of the monitoring of equipment and patient information during hemodialysis and security management, prior art hemodialysis monitoring apparatuses are superior; however, they are insufficient in view of labor saving in the overall processing relating to hemodialysis such as the priming before treatment (preparation process for washing and thereby cleaning the blood line and flow path or dialyser), blood withdrawal after needling (operation for starting extracorporeal circulation by withdrawal the blood from the body to the blood line), liquid replenishing during hemodialysis treatment, blood returning in the end (operation of finishing extracorporeal recirculation for returning the blood in the blood line to the body), smooth transitions between each process, and the like.

Automation has not been achieved especially in specific processes and transitions between processes, and thus labor intensive operations and expertise of medical professionals were needed. To finish the priming and blood withdrawal in a short time for a number of patients visiting at the same time, a large amount of manpower needed to be thrown in at a time. On the other hand, such placement of manpower was excessively large during hemodialysis treatment (blood circulation), thereby causing temporal non-uniformity in the content of labor, and economic inefficiency.

Moreover, in conventional hemodialysis practices, about 1 liter of intravenous formulation of saline was used for cleaning/filling the blood line and the hemodialyzer in the priming process. It has been pointed out that cleaning with the amount of 1 liter is not enough to sufficiently clean the flow path. However, use of a large amount of saline for cleaning/filling will cause an increase in costs.

Moreover, when a drop of blood pressure occurs during hemodialysis treatment, additional saline is needed thus complicating the routine and causing a cost increase. Recently, purifying technology of dialysate has made a remarkable progress, and a new system has been established in which an ultrapure purified dialysate is applied as a reverse-filtration liquid replenishing. In such a system, purified dialysate by means of a reverse filtration can be used in place of saline as a rinse liquid or a replenishing liquid. However, a liquid replenishing line system, which is capable of readily and reliably providing reverse-filtered dialysate for the purpose of replenishing during priming and treatment without resulting in a secondary contamination caused by stagnation of dialysate, has not been disclosed.

OBJECT OF THE INVENTION

It is an object of the present invention to solve the above described problems of the prior arts thereby enabling the rationalization (automation, simplification, labor saving, time saving, cost cutting) of hemodialysis treatment routines, of which rationalization was considered to be difficult because of their labor extensive nature and requirement of professional skills, and also to improve the safety of the treatment.

Thus, it is the object of the present invention to provide a hemodialyzing apparatus which allows the automation of most of the processes from treatment preparation to treatment completion in the above described hemodialysis treatment, unlike a conventional apparatus in which only part of each process is automated. That is, the object is to perform a series of processes from hemodialysis preparation to treatment completion safely, reliably and speedily, and to significantly reduce the labor costs and supply costs.

DISCLOSURE OF THE INVENTION

The present invention successfully achieved the object of labor saving in the operation of a hemodialyzing apparatus by providing an automatic hemodialyzing apparatus for purifying blood brought into contact with a dialysate via a semi-permeable membrane, comprising a hemodialyzer, a blood circulating system for circulating blood, and a dialysate supply/discharge system, characterized in that: the blood circulating system has an arterial line for withdrawal blood from the patient and feeding it into the hemodialyzer, and a venous line for returning blood flowing out from the hemodialyzer to the patient; the dialysate supply/discharge system has a dialysate supply line for supplying dialysate to the hemodialyzer, and a dialysate discharge line for discharging dialysate flowing out of the hemodialyzer; at least one of the two blood lines of said blood circulating system is provided with a reversibly-rotatable blood pump, and the other blood line is connected with a blood chamber and an overflow line having open/close means for making the liquid overflow from said blood chamber to the outside of the blood line; and said dialysate supply line and said dialysate discharge line have respectively first liquid supply means (supply side) and second liquid supply means (discharge side), at least one bypass line out of a first bypass line for linking the upstream side and the downstream side of the first liquid supply means or a second bypass line for linking the upstream side and the down stream side of the second liquid supply means being provided, and said bypass line(s) (the first bypass line and/or the second bypass line) being provided with third liquid supply means capable of supplying liquid both in forward and backward directions for enabling the regulation of the dialysate supply amount for water removing/liquid replenishing, wherein the supply speed of the third liquid supply means and the supply speed of the blood pump are regulatable in conjunction with each other.

In addition to the above described requirement for each configuration, it is preferable to provide open/close means in the upstream line or the downstream line, especially in the downstream line, of the overflow line linking part.

In the present specification, the upstream side or downstream side of the blood line is discriminated by the direction of blood flow during hemodialysis.

The present invention provides a hemodialyzing apparatus capable of automatically performing: a priming process before starting hemodialysis, a blood withdrawal process from the patient to the blood circulation system when starting hemodialysis, a starting mechanism for performing the transition from the blood withdrawal process to a hemodialyzing process, a hemodialyzing process, and a blood returning process for returning the blood to the patient from the blood circulation system, by controlling the said blood pump, the third liquid supply means, and the open/close means provided in the overflow line and the upstream line or the downstream line of the overflow line linking part.

Furthermore, the present invention provides a substantially fully automated hemodialyzing apparatus, which is not only capable of automating each process, but also capable of automatically performing the priming process before starting hemodialysis and, after connecting the arterial line and the venous line of the hemodialyzing apparatus, automatically and continuously performing each process or mechanism including; a blood withdrawal process from the patient to the blood circulation system when starting hemodialysis, a starting mechanism to perform the transition from the blood withdrawal process to a hemodialysis process, a hemodialysis process, and a blood returning process for returning the blood to the patient from the blood circulation system, by providing control means for controlling the blood pump, said third liquid supply means, and said open/close means in conjunction with one another and, by means of said control means, not only controlling each process separately but also controlling the processes so that transitions between each process can be performed without interruption.

Thus, in the hemodialyzing apparatus of the present invention, a blood pump provided in the blood circulation system, open/close means provided in the overflow line and the blood line of the blood chamber, particularly in the upstream side or downstream side of the vein chamber, especially in its downstream side, and the third liquid supply means for water removing/liquid replenishing provided in said bypass line of the dialysate supply/discharge system, are operated in conjunction with one another as shown in FIG. 2. This conjunctive control is not limited to each process but applied to the overall work flow including the transition mechanisms between each process thereby allowing easy and smooth operation of each process and transition between each process, and especially continuous operation of many processes. Thus, it is made possible not only to reduce the manual operation during the transitions of each process, but also to reduce operational errors.

The hemodialyzing apparatus of the present invention can be used for both removing water/replenishing liquid for the blood circulation system with a single liquid supply means, by providing a third liquid supply means capable of supplying liquid both forward and backward directions in at least one of a first bypass line bypassing the upstream side and downstream side of the first liquid supply means provided in the dialysate supply line, or a second bypass line bypassing the upstream side and the downstream side of the second liquid supply means provided in the dialysate discharge line.

That is, when a fluid pump is placed in the first bypass line provided on the supply side of the dialysate, and liquid is supplied in the same direction as the first liquid supply means (dialysate supply pump), the amount of dialysate flowing into the hemodialyzer becomes more than that of flowing out from the hemodialyzer and, as a result, liquid replenishing for the blood circulation system is performed. When liquid is supplied in the direction opposite to the above described direction, the inflow amount to the hemodialyzer becomes lower than the outflow amount from the hemodialyzer and, as a result, water removal from the blood circulation system is performed.

The above described mechanism may be similarly implemented by placing a fluid pump in the second bypass line provided on the side of dialysate discharge and by switching the liquid supply directions. In this case, when liquid is supplied in the same direction as the second liquid supply means (dialysate discharge pump), the amount of dialysate flowing out of the hemodialyzer becomes more than that of flowing into the hemodialyzer and, as a result, water removal from the blood circulation system is performed. And when liquid supply is performed in the opposite direction, the amount of liquid flowing out of the hemodialyzer becomes lower than the inflow amount of liquid and, as a result, liquid replenishing to the blood circulation system is performed. An embodiment in which a pump is provided in the second bypass line to perform liquid replenishing or water removing is preferably applied to a personal hemodialyzing apparatus which has a limitation on the flow rate of dialysate. When applying to a personal hemodialyzing apparatus, although a pump may be placed in the second bypass line alone, it is possible to increase the supply capacity of liquid replenishing or water removing by additionally placing a pump in the first bypass line.

In the above described embodiment for performing water removing or liquid replenishing, there is no need for a complicated structure for water removing/liquid replenishing. It is advantageous that the dialysate supply line and the bypass line has a simple structure, and that there is less chances of a stagnation in the dialysate flow by providing the above described third liquid supply means in either one of both bypass lines. That is, since the third liquid supply means provided in the dialysate supply system operates almost incessantly in all the processes of hemodialysis, there would be substantially no stagnation in the above described bypass line. With a flow being maintained in the line all the time, a secondary bacterial growth in the dialysate is prevented and thus potential endotoxin contamination can be avoided. Furthermore, by providing the above described third liquid supply means in the first bypass line, discharged dialysate would not flow in the bypass line and, as a result, there is no risk of contamination of the bypass line, or obstruction of the line due to wastes in the discharged liquid.

The above described third liquid supply means is preferably a reversibly-rotatable fluid pump of a constant volume type, its supply capacity is to be specified relating to the flow rate of the blood pump provided in the blood circulation system; a pump having a flow rate (liquid supply capacity) of 0 to 500 ml/min is preferable.

It is preferable to adjust the liquid supply amount of the third liquid supply means to be within the range of 1 to 2.5 times the liquid supply amount of the blood pump so that a part (about half) of dialysate which is filtered by a hollow fiber and flows into the blood line is fed into one blood line, and the remaining dialysate (the other half) is fed into the other blood line by the blood pump.

Moreover, the hemodialyzer of the present invention is preferably configured such that the reverse filtration speed of dialysate is changeable by the ultra-filtration ratio (UFR) of the hemodialyzer.

In the hemodialyzing apparatus according to the present invention;

(1) it is possible to perform automatic cleaning (priming) of the blood line by injecting dialysate into the blood line by reverse filtration via the hemodialyzer;

(2) it is also possible to perform blood withdrawal either from the arterial side alone or from both of the artery/vein at the same time by adjusting the liquid supply speeds of both of the blood pump and the third liquid supply means in conjunction with each other;

(3) it is made possible to perform blood withdrawal from the overflow line, in addition to the blood withdrawal by removing water via the hemodialyzer, which is disclosed in Japanese Patent application No. 11-138327 prior filed by the present applicant. That is, blood withdrawal by utilizing the overflow line is made possible by adjusting the liquid supply speed in conjunction with that of the above described blood pump, and by controlling the open/close means provided in said overflow line and either in the upstream line or the downstream line of the overflow line linking part.

(4) It is possible to perform cleaning of the blood line and removing air-bubbles effectively in the priming process by providing a blood pump in said arterial line and, in the venous line, a chamber to which an overflow line for overflowing liquid out of the blood line is connected, and open/close means such as valves in the upstream side or the downstream side of the chamber and in the overflow line. Also, in the blood returning process, it is possible to prevent the mixing of air, erroneous needling, and blood contamination, and it is also possible to reduce the workload of medical practitioners and perform blood returning rapidly and safely.

(5) It is possible to rapidly replenish liquid (by the above described reverse filtration) at any speed and by any amount by feeding dialysate to the blood line by operating the third liquid supply means during hemodialysis.

(6) It is possible to return blood in the arterial side and venous lines into the patient's body by means of the above described reverse filtration by controlling the third liquid supply means and the blood pump in conjunction with each other after the completion of hemodialysis, without detaching the blood line.

Out of the arterial line and/or the venous line, at least one of the blood lines is preferably provided with an air-bubble detection means. Providing this air-bubble detection means makes it possible to quickly detect an air-bubble mixed into blood and inform the operator of the need of any appropriate countermeasure Furthermore, in the hemodialyzer of the present invention, it is preferable that: an air reserve chamber in communication with the upper part of the blood chamber, especially that of the venous chamber via a connecting conduit is provided, and blocking means is provided in the connecting conduit; the connecting conduit has a branch part in communication with the vein pressure monitoring line in the connecting conduit between the blocking means and the venous chamber; and furthermore, a vein pressure monitoring line in communication with the upper part of the venous chamber is provided.

Adopting the above described configuration will make it possible to issue an alarm when the patient's vein pressure does not change within a predetermined range in a predetermined time after starting hemodialysis treatment.

Also, providing a flexible soft segment and a heparin injection segment in the above described arterial line and providing a pressure monitoring line in the venous line has an advantage in enabling the detection of abnormal conditions due to blood withdrawal failures, blood coagulation, narrowing or obstruction of blood line, etc. in their early stages.

In the present invention, an ultrapure dialysate is preferably used as the dialysate, and the hemodialyzing apparatus of the present invention is preferably fed with the ultrapure dialysate in a stable fashion during hemodialyzing operation. For example, it is possible to supply dialysate in a stable fashion by filtering a dialysate supplied from a normal hemodialyzing apparatus with an ultrafiltration filter provided in the entrance part of the hemodialyzing apparatus (H) relating to the present invention to remove impurities such as dissolved endotoxin and bacteria. Also, dialysate supplied from a typical dialysate production unit is preferably purified in advance conforming to a predetermined water quality standard (for example, Kyushu HDF investigative commission's bulletin, 1, 33-42, 1995).

BRIEF DESCRIPTION OF THE DRAWINGS

FIGS. 1 and 2 show an automatic priming process in which the flow paths of the hemodialyzer D and the venous chamber C are cleaned while discharging the liquid in the paths from the overflow line L3. FIG. 2 further shows control means G which is capable of gang controlling the blood pump (P1), water removing/liquid replenishing pump (P4), and the valve 2 (PV2) which is the open/close means for venous line and valve 1 (PV1) which is the open/close means for the overflow line, and the transfer system g which links the forgoing components FIG. 3 shows an automatic priming process in which the arterial line L1 and a part of the venous line L2 extending from the connecting part 2 to the venous chamber C is cleaned while discharging dialysate from the overflow line L3.

FIG. 4 shows an automatic priming process in which the entire blood line is cleaned while discharging liquid from the overflow line L3 by circulating a half amount of the dialysate supplied into the blood line by the water removing/liquid replenishing pump P4 to the upstream side of the hemodialyzer, and the other half amount of the dialysate to the downstream side of the hemodialyzer.

BEST MODE FOR CARRYING OUT THE INVENTION

The hemodialyzing console M is a dialysate flow rate regulator, and also a blood flow rate regulator. The hemodialyzing console M has typical performances as a dialysate supply mechanism having a closed system.

The console (M) is provided with third liquid supply means (hereinafter referred to as water removing/liquid replenishing pump (P4)) to realize a function of water removing/liquid replenishing from/to the blood circulation system by a reverse filtration of the hemodialyzer.

Figure 1:
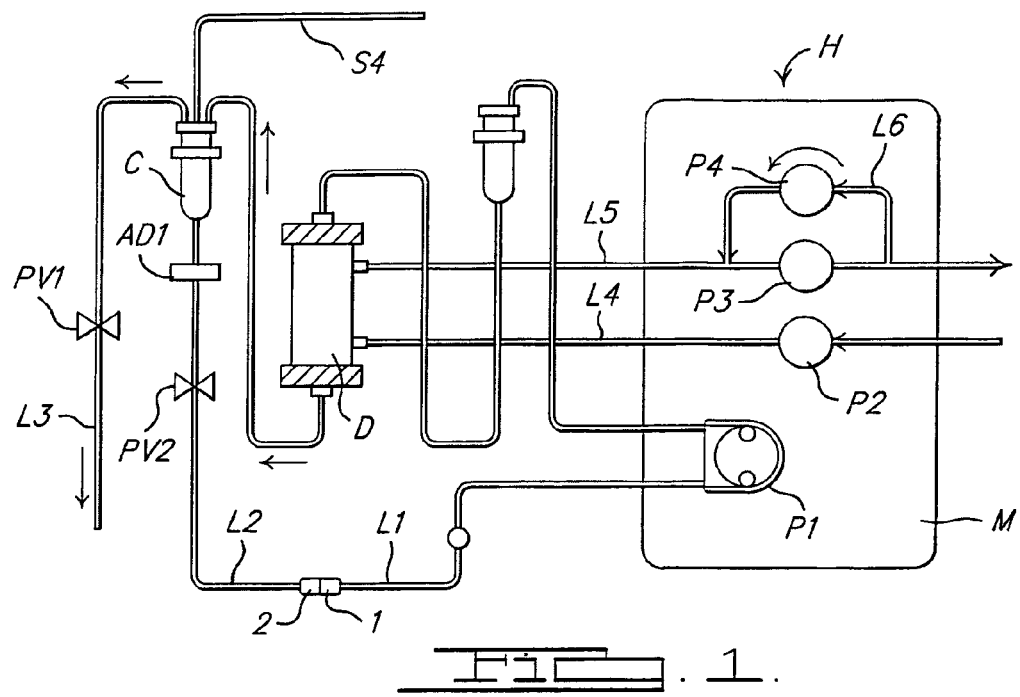
FIGS. 1 to 4 are schematic diagrams to show the configuration of the hemodialyzing apparatus of the present invention and the automatic priming process by use of the hemodialyzing apparatus.

The water removing/liquid replenishing pump (P4) may be provided, as shown in FIG. 1, either in the second bypass line L6 on the side of the dialysate discharge line L5, or in the bypass line which is provided in the dialysate supply line L4, between the upstream side and the downstream side of the dialysate supply pump (P2) so as to link them. Further, both bypass lines mentioned above may be provided with a water removing/liquid replenishing pump.

The water removing/liquid replenishing pump (P4) is a fluid pump capable of switching the ejection direction into forward and backward directions and of regulating the flow rate within a range of, for example, about 0 to 500 ml/min, preferably about 0 to 200 ml/min.

In each figure, L1 indicates an arterial line and L2 a venous line, both of them constituting a blood line. The arterial line (L1) has a connecting part (1) with the arterial side paracentesis needle and a connecting part with the hemodialyzer D.

The blood line is provided with a blood pump (P1) which is capable of controlling forward and backward revolution to maintain an extracorporeal circulation. Also the blood line preferably has an air-bubble detector (AD1).

The blood line is preferably provided with an air-bubble detector (AD1). The air-bubble detector (AD1) is provided, for example, in the downstream side of the venous chamber so that when air is sensed while returning blood, the blood pump (P1) is immediately stopped and the valve (PV2) is closed to prevent air being erroneously injected into the body.

The venous line (L2) consists of a connecting part with the hemodialyzer D, a venous chamber (C), an overflow line (L3) and vein pressure (blood pressure) monitoring line (S4) which are in communication with the upper part of the venous chamber, and a connecting part (2) with the venous side paracentesis needle.

PV1 and PV2 represent valves, and these two valves relate to the operation or control of automatic priming process, automatic blood withdrawal process, and automatic blood returning process.

The valve 2 (PV2) is provided in the venous line on the upstream side or the downstream side of the venous chamber, especially on its downstream side, and the valve 1 (PV1) is provided in the overflow line (L3).

Figure 2:
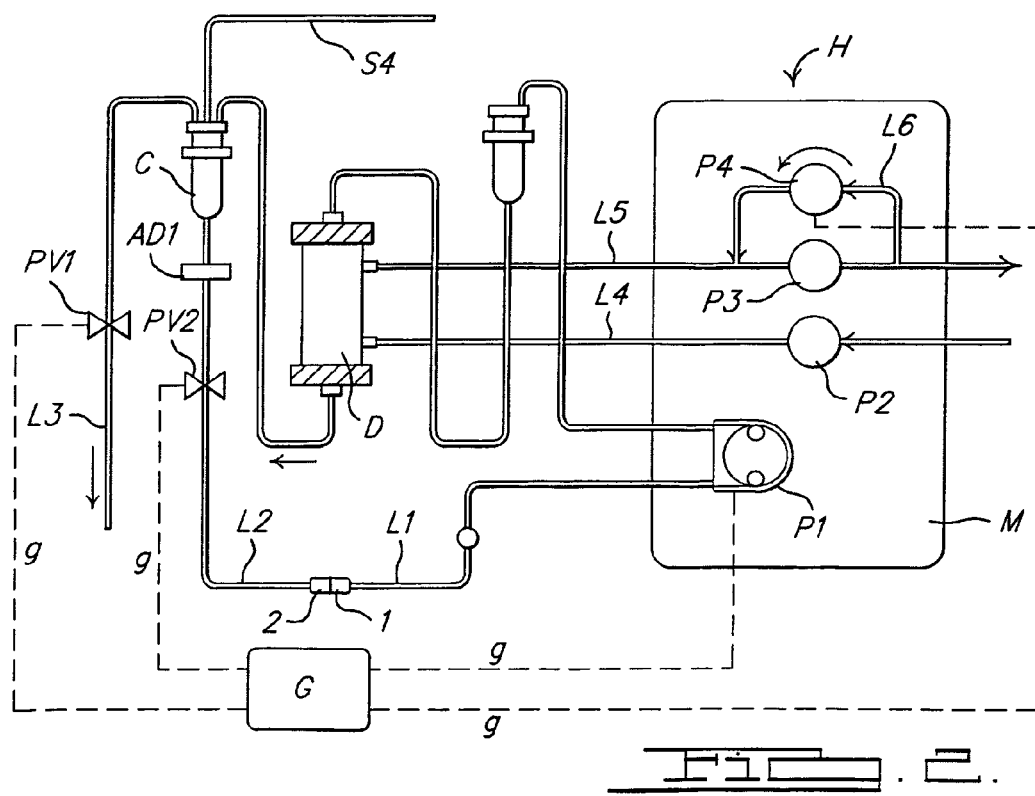

For the automation of the hemodialyzing apparatus of the present invention, it is essential to gang control, as described above, the blood pump (P1), the water removing/liquid replenishing pump (P4), and the valve 2 (PV2) which is the open/close means for the venous line and the valve 1 (PV1) which is the open/close means for the overflow line. The control means G in FIG. 2 is capable of operating these components in conjunction with each other via the transfer system g which links these components, and also controlling each component responding to the changes of the other components.

The control means G is preferably provided in a hemodialyzing console which contains various monitors and safety devices for general hemodialyzing apparatuses.

In the automatic priming process using the automatic hemodialyzing apparatus of the present invention, it is possible to remove air accumulated in the venous chamber by performing chucking (flushing) operation by opening/closing the valve 2 (PV2) when injecting and recirculating the liquid during the automatic priming process. After finishing the automatic priming process, tip parts 1, 2 of the blood line are detached, and each tip part is connected to the vein and artery of the patient. At this moment, in the venous line, the liquid in the line will flow out when the tip part is detached. Therefore, valve 2 (PV2) is closed to prevent the leakage of liquid.

The reverse filtration speed during automatic priming is significantly affected by the ultra-filtration rate (UFR) of the hemodialyzer. When a hemodialyzer with a low UFR is subjected to a high reverse filtration pressure, an alarm of abnormal liquid pressure will be issued. Therefore, it is preferable to modify the reverse filtration speed in response to the measured UFR at the hemodialyzing apparatus. The modification is made through a feedback control of UFR, and after the reverse filtration speed is stabilized, a maximum reverse filtration speed in subsequent processes (liquid replenishing/blood returning) is set at a stable index during priming.

In the blood returning process using the hemodialyzing apparatus of the present invention, in order to reduce the amount of dialysate through reverse filtration as much as possible, it is necessary to lower the amount of blood, or liquid level, left in the venous chamber during blood returning. To this end, the following configuration is preferable.

Figure 8:
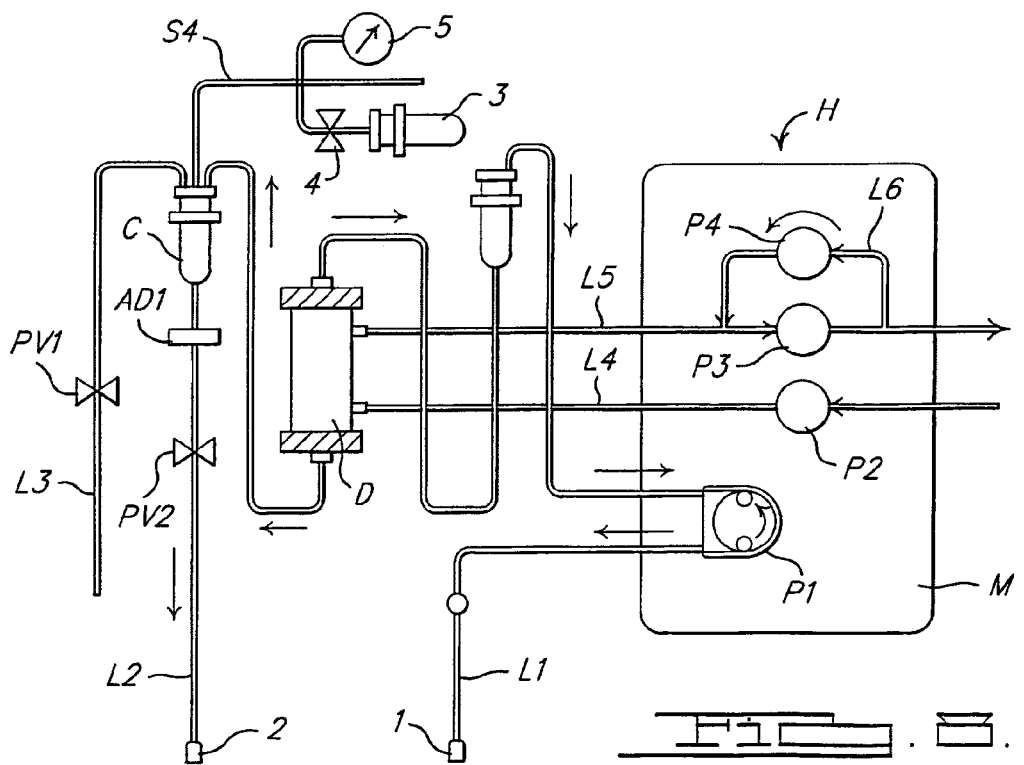
FIG. 8 shows an automatic blood returning process.

That is, an air reserve chamber 3 is provided which is in communication with the upper part of the venous chamber via a connecting conduit, and the connecting conduit is provided with air blocking means 4. Also, as shown in FIG. 8, a branch part in communication with the vein pressure monitor 5 may be provided in the connecting conduit between the blocking means and the venous chamber.

When performing automatic priming, the blocking means is opened to fill the air reserve chamber with air. During blood withdrawal and hemodialyzing processes, the blocking means is closed to keep the chamber filled with air. Then, upon starting blood returning, it is possible to lower the liquid level of the venous chamber by opening the blocking means so as to feed the air stored in the air reservoir into the venous chamber.

Moreover, in the hemodialyzing method using the hemodialyzing apparatus of the present invention, if the vein pressure monitoring line is kept closed after starting hemodialysis, the vein pressure can not be measured and therefore the alarm function will not work. For this reason, it is also preferable to give the hemodialyzer of the present invention a function of detecting the obstruction of the vein pressure monitoring line. A possible configuration for adding a function of detecting an obstruction of the vein pressure monitoring line during hemodialyzing process is as follows. It may be judged that an obstruction of the vein pressure monitoring line has occurred and issuing an alarm is needed, when the vein pressure measurement does not vary within a predetermined range for a predetermined time after hemodialyzing is started despite the fact that the vein pressure measurements should necessarily vary due to the pulsation caused by the blood pump.

Hereinafter, the best embodiments of the present invention will be described in more detail.

(1) Automatic Priming Process

A loop is formed by connecting the arterial line L1 and the venous line L2 of the blood line. The dialysate lines L4, L5 are connected to the hemodialyzer D. The console M starts operating in a preparation mode (a mode in which air is removed from the apparatus and the lines, and replacement of liquid with dialysate (substitute fluid) is performed). Upon completion of the preparation, the valve 1 (PV1) is opened and the valve 2 (PV2) is closed while keeping the blood pump P1 stopped. The water removing/liquid replenishing pump P4 is backwardly rotated at 200 ml/min by internal setting to supply substitute fluid into the blood line via the hemodialyzer D. Through this operation, the flow path between the hemodialyzer D and the venous chamber C is cleaned by discharging the liquid in the foregoing flow path from the overflow line L3 (see FIGS. 1 and 2).

The pump P2 and pump P3 of the dialysate lines L4, L5 is controlled in such a way that the liquid supply amount and the liquid discharge amount are synchronized.

Figure 3:
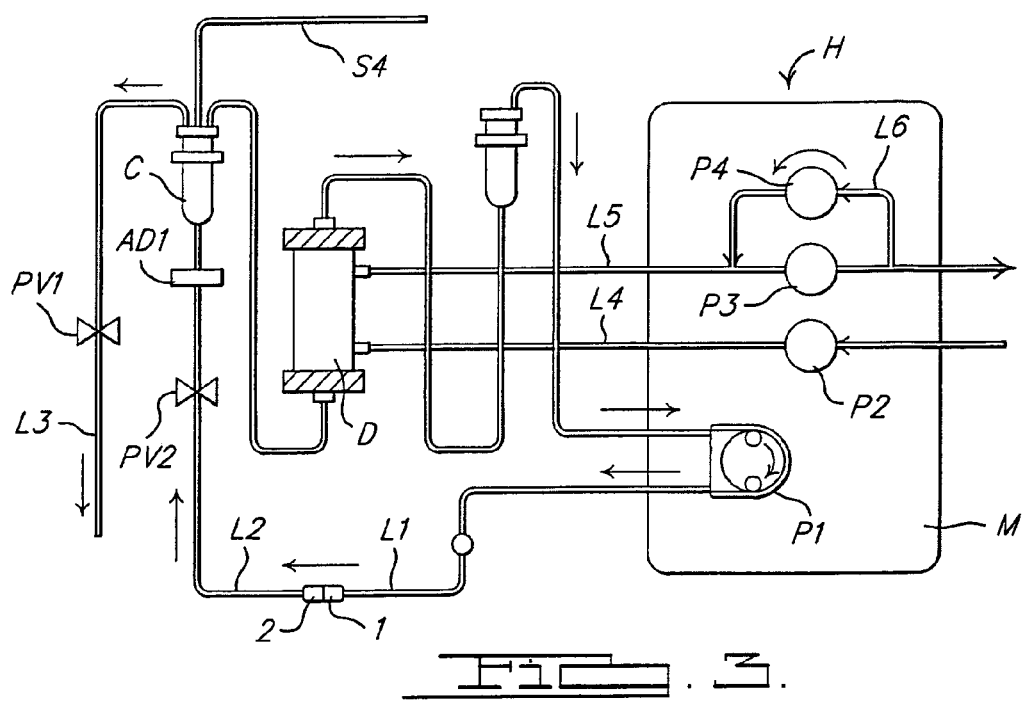

With the valve 1 (PV1) and the valve 2 (PV2) being opened, the water removing/liquid replenishing pump 4 is backwardly rotated at 200 ml/min by internal setting to feed dialysate into the blood line (liquid replenishing). And the blood pump 1 is backwardly (opposite to the liquid supply direction of the blood pump during hemodialysis) rotated at 200 ml/min as with the pump P4 thereby cleaning the arterial line L1 and the part of the venous line L2 from the connecting part 2 to the venous chamber C while discharging from the overflow line L3 the dialysate supplied into the blood line by the water removing/liquid replenishing pump 4 (FIG. 3).

Figure 4:
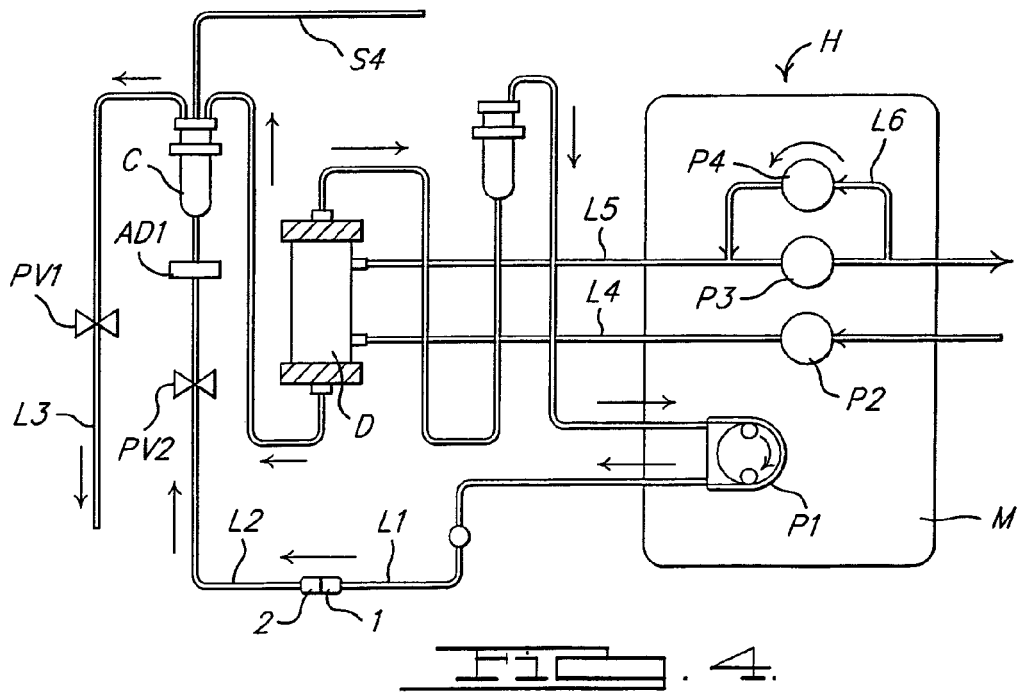

With the valve 1 (PV1) and valve 2 (PV2) being opened, the blood pump 1 is backwardly rotated setting its liquid supply speed at 50% of that of the water removing/liquid replenishing pump 4, or 100 ml/min (internal setting). Also, the entire blood line is cleaned while discharging the liquid from the overflow line L3 by backwardly rotating the water removing pump at 200 ml/min (internal setting) to circulate a halt amount of the dialysate replenished by the pump into the upstream side of the hemodialyzer, and the other half amount of the dialysate into the downstream side of the hemodialyzer (FIG. 4).

With the valve 1 (PV1) being closed, the valve 2 (PV2) is opened to stop the water removing/liquid replenishing pump 4. The blood pump P1 is kept rotating in the forward direction at a liquid supply speed of 350 ml/min (internal setting) in a waiting mode. Alternatively, the blood pump is stopped after a predetermined time has elapsed to complete the priming process.

(2) Automatic Blood Withdrawal Process (Blood Withdrawal with High-Performance Water Removing)

By blocking the blood line near the artery and vein connecting parts 1, 2, e.g. with clamps, both connecting parts are detached and connected to the paracentesis needles (AFV etc.) pierced into the patient body after removing the air remained in the connecting part. After removing the forceps blocking the line, the switch button for automatic blood withdrawal is pressed thereby shifting the operation mode into a blood withdrawal mode.

Figure 5:
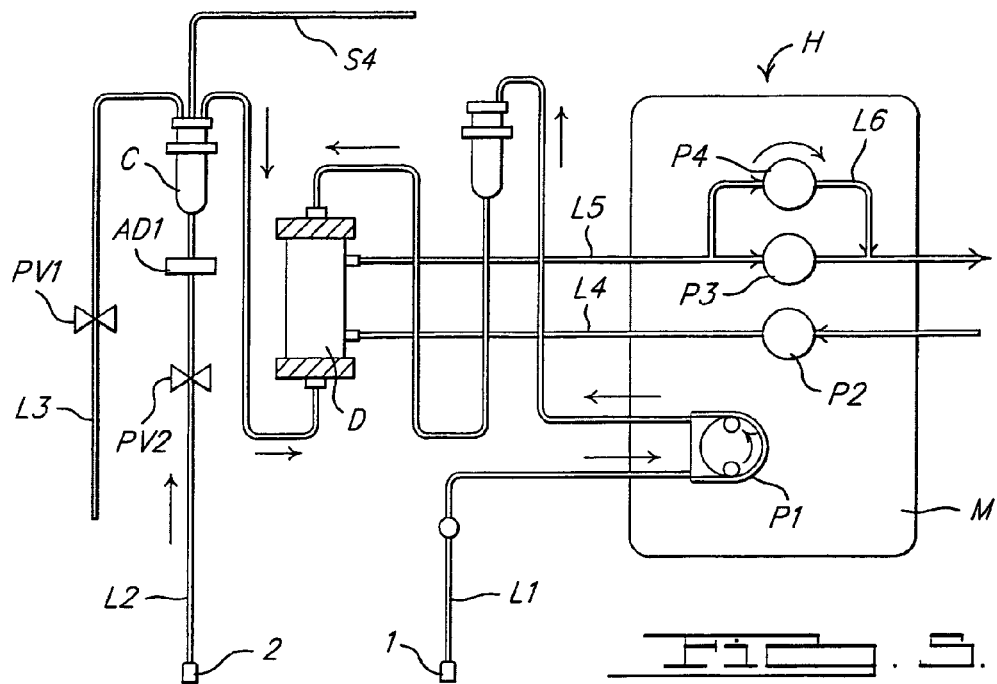
FIG. 5 shows an automatic blood withdrawal process blood withdrawal with high-performance water removing.
Figure 6:
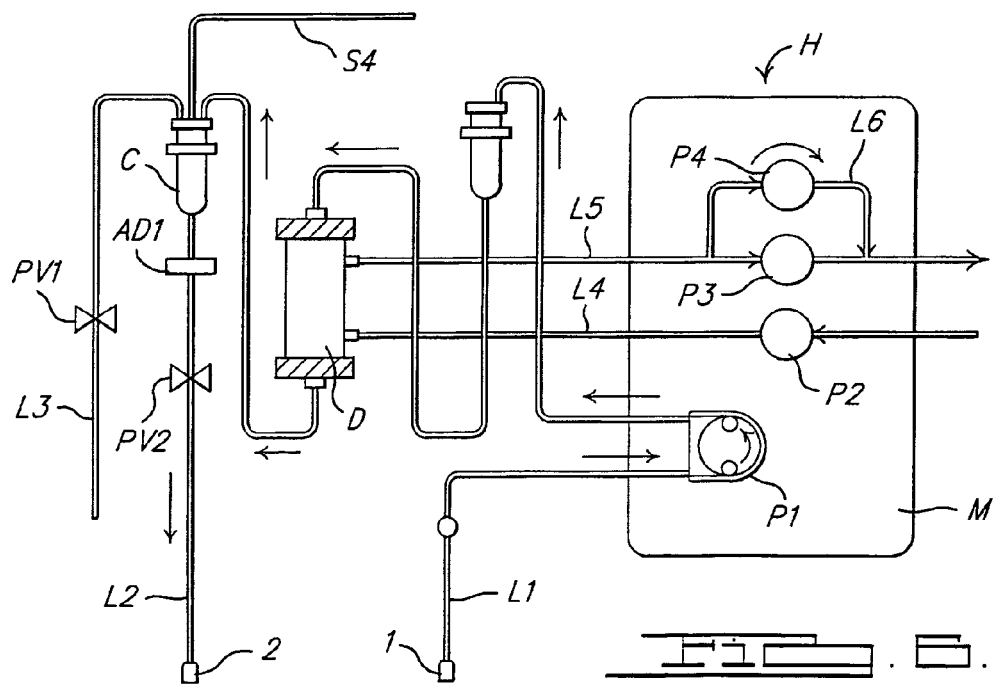
FIG. 6 shows a hemodialyzing process.

With the valve 1 (PV1) closed and the valve 2 (PV2) opened, the water removing/liquid replenishing pump 4 is rotated in the forward direction at 100 ml/min (internal setting). Also, the blood pump P1 is rotated in the forward direction at 50 ml/min (internal setting). A time period in which water is removed from the filling liquid (dialysate) in the blood line through the hemodialyzer and the filling liquid (dialysate) in the blood line is replaced by blood is set (for example 1 min) in advance, and blood withdrawal is to be completed when the predetermined time has elapsed. As soon as the blood withdrawal is completed, the operation mode is shifted to a normal hemodialyzing mode automatically or manually (FIG. 5).

In the case of the present blood withdrawal process, blood is withdrawn from the artery at a rate of 50 ml/min by the rotation of the blood pump P1 at 50 ml/min (internal setting), and also 50 ml/min of blood, which is the amount of blood corresponding to the difference in the rotation between the water removing/liquid replenishing pump P4 and the blood pump P1 (that is 100 ml/min-50 ml/min), is withdrawn from the vein (3) Automatic Blood Withdrawal Process (by Overflow Discharge)

As with the above described blood withdrawal with high-performance water removing, while the blood line is blocked near the artery/vein connecting parts 1, 2, e.g. by means of clamps, both connecting parts 1, 2 are detached and connected to the paracentesis needles (AvF etc.) pierced into the patient body after removing the air existing in the connecting parts. Then, with the forceps blocking the line being removed, the automatic blood withdrawal button is pressed thereby shifting the operation mode into an automatic blood withdrawal mode.

Figure 7:
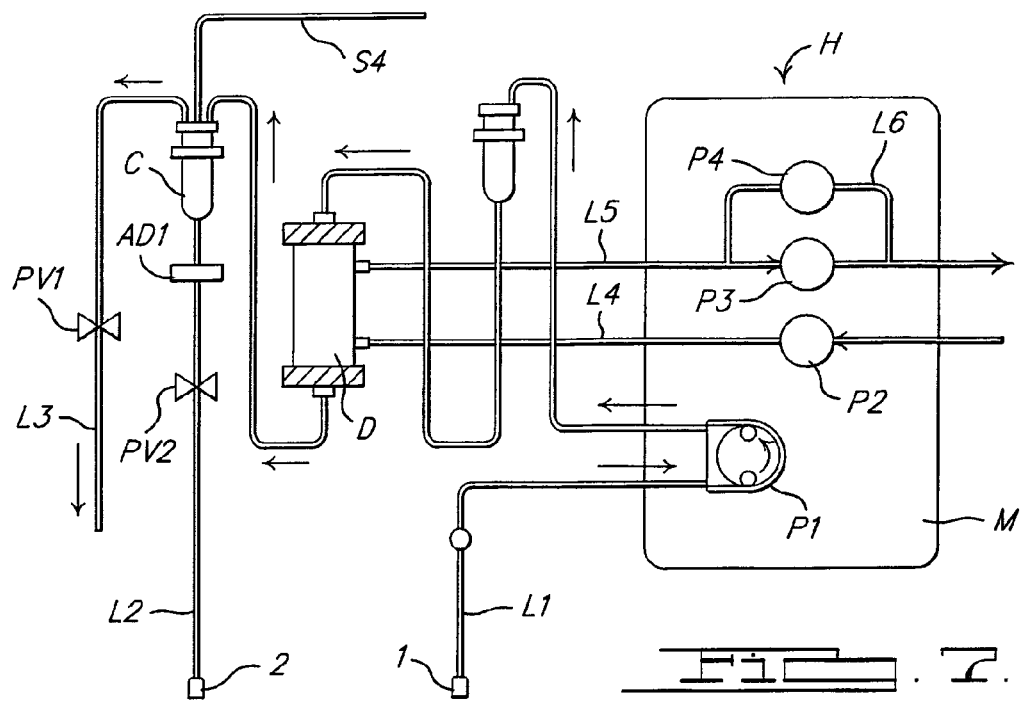
FIG. 7 shows an automatic blood withdrawal process (based on overflow discharge).

With the valve 1 (PV1) opened, the valve 2 (PV2) closed, and the water removing/liquid replenishing pump 4 (PV4) being at a halt, the blood pump 1 (PV1) is forwardly rotated at 100 ml/min (internal setting). Thereafter, as with the blood withdrawal process with high-performance water removing, blood withdrawal process is continued until the filling liquid (dialysate) in the blood line is replaced with blood (FIG. 7).

In the hemodialyzing apparatus of the present invention, in a state in which blood withdrawal from the vein such as a cutaneous vein is impossible in the blood withdrawal process, the operation is controlled in such a way that when the dialysate pressure becomes a negative excessive pressure, operation is automatically shifted to a blood withdrawal operation which is performed only from the arterial side (it is possible to judge a negative excessive pressure in vein pressure at the same time).

(4) Hemodialyzing Process

In the hemodialyzing process, with valve 1 (PV1) closed and the valve 2 (PV2) opened, the blood pump P1 and the water removing/liquid replenishing pump P4 are forwardly driven at a predetermined flow rate. The valve 2 (PV2) is in conjunction with the air-bubble detector AD1, and is stopped as soon as an air-bubble is detected in the blood line. The blood pump P1 is also stopped at the same time.

(5) Automatic Blood Returning Process

With water removing being finished and the target hemodialysis time having elapsed, operation is shifted to the automatic blood returning mode either automatically or by pressing the automatic blood returning button. With valve 1 (PV1) closed and the valve 2 (PV2) opened, the water removing/liquid replenishing pump P4 is backwardly rotated at 200 ml/min (internal setting) and the blood pump P1 is backwardly rotated at 100 ml/min (internal setting) which is 50% of the rate of the water removing pump. By the above mentioned ratio of flow rate, blood is removed from the arterial side at a rate of 100 ml/min by the pump P1, and from the venous side at a rate of 100 ml/min which is determined by the difference in the rotational speed between the water removing/liquid replenishing pump P4 and the foregoing blood pump P1 (200 ml/min 100 ml/min). After the predetermined time has elapsed, or when the remaining blood in the blood line has been replaced with dialysate (cleaning liquid), the blood pump P1 and the water removing/liquid replenishing pump P4 are stopped completing the automatic blood returning process (FIG. 8).

In a blood returning state, an obstruction in the vein pressure monitoring line side can be determined from the increase in the vein pressure. However, an obstruction of the arterial side is determined in the following manner since there is no artery pressure monitor provided.

After starting blood returning, pressure measuring means which can measure the dialysate pressure in the dialysate line and the vein pressure in the venous line are used to start monitoring each of the foregoing pressures from the moment when the dialysate pressure and vein pressure are stabilized so that a potential obstruction of the arterial side is determined from a increasing trend in each of the foregoing pressures from the stabilized state.

As can be seen clearly from each of the above described processes, the present invention can provide so called fully automated hemodialyzing apparatus whereby every process of hemodialysis is automated except the process for connecting the hemodialyzing apparatus of the present invention to the paracentesis needles (AVF etc.) pierced into the patient's body.

INDUSTRIAL APPLICABILITY

The hemodialyzing apparatus and hemodialyzing method of the present invention have very wide industrial applicability in the fields of blood hemodialyzing apparatuses and hemodialyzing methods as shown below.

(1) According to the hemodialysis monitor and the dedicated blood line relating to the present invention, it is made possible to automate the priming process, to simplify the operation in the blood withdrawal process, to prevent the inflow of the priming liquid into the patient's body, and to automate by programming a series of treatment processes including blood withdrawal/hemodialysis starting/recovery/treatment completing processes. This enables significant reduction of the total time spent by medical personnel at bedside, and contributes to the enhancement of efficiency and labor saving in medical practices relating to hemodialysis treatment.

(2) It is also made possible to facilitate the extraction operation of the artery/vein needles upon completion of hemodialysis and to reduce the frequency of blood contamination. Since a series of operations are significantly simplified, there is no need for professional skills of hemodialysis practitioners as needed before. Also since a sufficient amount of reverse filtration dialysate is used for cleaning in the priming process, cleaning is performed more fully than the one by use of usual saline of 1 L, thus the cleanness of the extracorporeal circulation line is improved. Moreover, upon occurring a blood pressure drop during treatment, liquid replenishing may be performed rapidly and conveniently. It is also an economic advantage that saline is not used for priming or liquid replenishing. As so far described, the present invention is expected to significantly contribute to the enhancement of efficiency, labor saving, safety, cost reduction in hemodialysis treatments.

(3) In the hemodialyzing apparatus relating to an embodiment of the present invention, since a single pump is utilized both for water removing and for reverse filtration liquid replenishing of dialysate, the water removing/liquid replenishing pump (P4) is being operated either forwardly or backwardly in any of priming/blood withdrawal/hemodialysis treating/blood returning processes, and therefore there is substantially no stagnation in the flow path of the water removing/liquid replenishing bypass line, and also there is no risk of growth of bacteria in the line.

The invention claimed is:

1. An automatic hemodialyzing apparatus for purifying blood brought into contact with dialysate via a semi-permeable membrane, the apparatus having a hemodialyzer, a blood circulating system for circulating blood, and a dialysate supply/discharge system for supplying/discharging dialysate, the apparatus comprising:

the blood circulating system has two blood lines, one being an arterial line for withdrawing blood from the patient and feeding it into the hemodialyzer, and the other blood line being a venous line for returning the blood flowing out from the hemodialyzer to the patient;

the dialysate supply/discharge system has a dialysate supply line for supplying dialysate to the hemodialyzer, and a dialysate discharge line for discharging the dialysate flowing out of the hemodialyzer;

one of the two blood lines of said blood circulating system is provided with a reversibly-rotatable blood pump, and the other blood line is provided with a blood chamber and an overflow line having open/close means for making the liquid overflow from said blood chamber to the outside of the blood line; and said dialysate supply line and said dialysate discharge line have respectively first liquid supply means (supply side) and second liquid supply means (discharge side), at least one bypass line out of a first bypass line for linking the upstream side and the downstream side of the first liquid supply means or a second bypass line for linking the upstream side and the down stream side of the second liquid supply means being provided, and said bypass line(s) (the first bypass line and/or the second bypass line) being provided with third liquid supply means capable of supplying liquid both in forward and backward directions for enabling the regulation of the dialysate supply amount for water removing/liquid replenishing.

2. The hemodialyzing apparatus according to claim 1, characterized in that said hemodialyzing apparatus is provided with an air reserve chamber, which is in communication with the upper part of the blood chamber via a connecting conduit, and said connecting conduit is provided with air blocking means.

3. The hemodialyzing apparatus according to claim 2, characterized in that the blood chamber is a venous chamber.

4. The hemodialyzing apparatus according to claim 3 characterized in that a branch part which is in communication with a vein pressure monitor is provided in said connecting conduit between said blocking means and the venous chamber.

5. The hemodialyzing apparatus according to claim 2, characterized in that said hemodialyzing apparatus is provided with a vein pressure monitoring line in communication with the upper part of the venous chamber, and is adapted to issue an alarm when the vein pressure of the patient does not vary within a predetermined range for a predetermined time after hemodialyzing has been started.

6. The automatic hemodialyzing apparatus according to claim 1, characterized in that a liquid supply amount of the third liquid supply means can be regulatable within a range of 1 to 2.5 times a liquid supply amount of the blood pump.

7. The hemodialyzing apparatus according to claim 1, characterized in that a reverse filtration speed, at which dialysate is reverse-filtered from said dialysate supply/discharge line to said blood line via the hemodialyzer by supplying the dialysate of the third liquid supply means, is changeable in accordance with the ultrafiltration rate (UFR) of said hemodialyzer.

8. The hemodialyzing apparatus according to claim 1, characterized in that each process or mechanism including a priming process before starting hemodialysis, a blood withdrawal process from the patient to the blood circulation system when starting hemodialysis, a starting mechanism for performing the transition from the blood withdrawal process to a hemodialysis process, a hemodialyzing process, and a blood returning process for returning blood to the patient from the blood circulation system when finishing hemodialysis can be performed automatically by controlling the blood pump, the third liquid supply means, and the open/close means provided in the overflow line and the upstream line or the downstream line of the overflow linking part.

9. The hemodialyzing apparatus according to claim 1, characterized in that the blood withdrawal process is performed by discharging the liquid, with which the blood line is filled, from the overflow line.

10. The hemodialyzing apparatus according to claim 1, characterized in that the blood withdrawal process is performed in such a way that the liquid filling the blood line is discharged to the outside of die blood line through water removal by the hemodialyzer.

11. The hemodialyzing apparatus according to claim 1, characterized in that in a state in which blood withdrawal from a vein such as cutaneous vein cannot be performed in the blood withdrawal process, it can be controlled in such a way that operation is automatically shifted to blood withdrawal from the arterial side alone when the dialysate pressure becomes an excessively negative state after the blood withdrawal operation has been started.

12. The hemodialyzing apparatus according to claim 1, characterized by comprising control means for controlling, in conjunction with one another, the blood pump, the third liquid supply means, and the open/close means provided in the overflow line and the upstream line of the overflow line linking part.

13. The hemodialyzing apparatus according to claim 1, characterized in that the priming process before starting hemodialysis an automatically be performed, and after connecting the arterial line and the venous line of the hemodialyzing apparatus, each process or mechanism including:

a blood withdrawal process from the patient to the blood circulation system when starting hemodialysis;

a starting mechanism for performing the transition from the blood withdrawal process to a hemodialyzing process; a hemodialysis process; and a blood returning process for returning blood to the patient front the blood circulation system when finishing hemodialysis; can be performed automatically and continuously.

14. The hemodialyzing apparatus according to claim 1, characterized by comprising pressure measuring means capable of measuring the dialysate pressure in the dialysate line and the vein pressure in the vein line, whereby an obstruction in the arterial side can be detected based on an increasing trend in each of the dialysate pressure and the vein pressure from a stable state by starting the monitoring of said pressures from the moment when they are stabilized after blood returning has been started.

15. The apparatus of claim 1 wherein the other blood line is provided with and an open/close means at a downstream side or an upstream side of the blood chamber.

16. The apparatus of claim 15 further comprising a control means which controls at least the blood pump, the third liquid supply means, and the open/close means provided on the overflow line and on the blood line downstream or upstream of the blood chamber, in conjunction with each other.

17. A priming method characterized in that a priming process is performed by connecting the arterial line and the venous line of the hemodialyzing apparatus according to claim 1, and controlling the blood pump, the third liquid supply means, and the open/close means provided in the overflow line and the upstream line of the overflow line linking part.

18. The priming method according to claim 17, characterized in that the priming process is performed by changing the reverse filtration speed, at which dialysate is reverse-filtered from the dialysate supply/discharge line to said blood line via the hemodialyzer by supplying the dialysate of the third liquid supply means, in accordance with the ultrafiltration rate (UFR) of said hemodialyzer.

19. The priming method according to claim 18, characterized in that the priming process is performed by using ultrapure dialysate.

* * * * *